(12) United States Patent
Kober et al.

(10) Patent No.: US 6,831,041 B2
(45) Date of Patent: Dec. 14, 2004

(54) OIL SUSPENSION CONCENTRATES BASED ON A CYCLOHEXENONE OXIME ETHER LITHIUM SALT AND THE USE THEREOF AS PLANT PROTECTION AGENTS

(75) Inventors: Reiner Kober, Fussgönheim (DE); Rainer Berghaus, Speyer (DE); Thomas Kröhl, Mainz (DE); Hans Ziegler, Mutterstadt (DE); Volker Maywald, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/380,120

(22) PCT Filed: Sep. 12, 2001

(86) PCT No.: PCT/EP01/10537
§ 371 (c)(1),
(2), (4) Date: Mar. 11, 2003

(87) PCT Pub. No.: WO02/21921
PCT Pub. Date: Mar. 21, 2002

(65) Prior Publication Data
US 2004/0097374 A1 May 20, 2004

(30) Foreign Application Priority Data
Sep. 13, 2000 (DE) ......................................... 100 45 130

(51) Int. Cl.$^7$ .............................................. A01N 43/18
(52) U.S. Cl. ....................................... 504/288; 504/363
(58) Field of Search ................................. 504/288, 363

(56) References Cited

U.S. PATENT DOCUMENTS

| | | | |
|---|---|---|---|
| 5,411,932 A | 5/1995 | Yoshida et al. | 504/132 |
| 5,981,440 A | 11/1999 | Bratz et al. | 504/344 |
| 6,087,305 A | 7/2000 | Kober et al. | 504/313 |
| 6,133,202 A | 10/2000 | Bratz et al. | 504/244 |
| 6,383,987 B1 | 5/2002 | von der Heyde et al. | 504/271 |

FOREIGN PATENT DOCUMENTS

| | | | |
|---|---|---|---|
| DE | 197 01 123 | * | 8/1997 |
| EP | 0266068 | | 5/1988 |
| EP | 0313317 | | 4/1989 |
| EP | 0394847 | | 10/1990 |
| WO | 97/20807 | * | 6/1997 |
| WO | 00/35288 | * | 6/2000 |

* cited by examiner

Primary Examiner—S. Mark Clardy
(74) Attorney, Agent, or Firm—Keil & Weinkauf

(57) ABSTRACT

The present invention relates to oil suspension concentrates based on 2-{1-[2-(4-chlorophenoxy)propoxyimino]butyl}-3-hydroxy-5-(tetrahydrothiopyran-3-yl)cyclohex-2-enone lithium salt and certain formulation auxiliaries and to the use of the oil suspension concentrates as crop protection compositions and in particular as rice herbicides. Preferred formulation auxiliaries are mono- and/or dicarboxylic esters, for example fluid fatty acid esters, anionic surfactants of the sulfonate type, for example alkyl- and alkylarylsulfonates and also sulfosuccinates, and nonionic surfactants of the type of the nonethoxylated or ethoxylated carboxylic acids and esters of mono- or polyfunctional alcohols, for example ethoxylated fatty acids and polyoxyethylene sorbitan fatty acid esters.

The oil suspension concentrates described herein are storage-stable and have excellent use properties.

10 Claims, No Drawings

OIL SUSPENSION CONCENTRATES BASED ON A CYCLOHEXENONE OXIME ETHER LITHIUM SALT AND THE USE THEREOF AS PLANT PROTECTION AGENTS

Oil suspension concentrates based on a cyclohexenone oxime ether lithium salt and their use as crop protection compositions.

The present invention relates to oil suspension concentrates based on 2-{1-[2-(4-chlorophenoxy)propoxyimino] butyl}-3-hydroxy-5-(tetrahydrothiopyran-3-yl)cyclohex-2-enone lithium salt and certain formulation auxiliaries, and to the use of the oil suspension concentrates as crop protection compositions, in particular as rice herbicides.

In addition to the optimization of the properties of an active compound, it is particularly important, with a view to an industrial production and use of these active compounds, to develop an efficient crop protection composition. By formulating the active compound appropriately, an optimum balance of in some cases opposed properties such as biological activity, toxicity, possible effects on the environment and costs has to be found.

In addition, the formulation has a considerable effect on the stability of a crop protection composition. This is particularly important in cases where, owing to instabilities of the active compounds or unfavorable storage conditions, the relevant requirements that a crop protection composition has to meet are particularly high.

Suspension concentrates, for example, are of great practical importance. They are liquid heterogeneous formulations of solid active compound in a liquid phase. In addition to general advantages of liquid formulations with respect to handling and meterability, for example under ULV (ultra low volume) conditions, suspension concentrates additionally frequently have good biological activity combined with relatively low phytotoxicity. Aqueous suspension concentrates are typical. However, individual cases of oily suspension concentrates have also been described, but there is the problem that many active compounds and active compound salts are soluble in the oily phase which is usually used.

Thus, WO 00/35288 describes the formulation of glyphosates or glufosinates together with cyclohexenone oxime ethers as oil suspension concentrates. In addition to the free acids, salts of the cyclohexenone oxime ethers are also considered here. However, in experiments these have been found to be unsuitable, owing to insufficient stability, as shown by the formulation of the lithium salt of 2-{1-[2-(3-chloroallyloxy)iminopropyl]-butyl}-3-hydroxy-5-(tetrahydropyran-3-yl)cyclohex-2-enone together with calcium glyphosate.

EP 0 313 317 describes oily suspension concentrates of certain sulfonylurea derivatives which can also be used in the form of their alkali metal, alkaline earth metal or ammonium salts. Vegetable oils, especially corn oil, and surfactants capable of emulsifying the vegetable oils in water are used. Similar oil-based suspension concentrates are described in U.S. Pat. No. 5,411,932. Here, too, vegetable oils, in particular corn oil and rapeseed oil, and additionally also mineral oils, and also surfactants are used for formulating a certain sulfonamide, i.e. nicosulfuron, or a salt thereof. The stability of the liquid sulfonylurea formulations, which is insufficient per se, is improved by adding urea.

Cyclohexenone oxime ethers and their metal salts are generally known useful crop protection agents. They are held in high esteem, especially as grass herbicides. The cyclohexenone oxime ether of formula (Ia) below and metal salts thereof (WO 97/20807) have been found to be particularly suitable herbicidally active compounds:

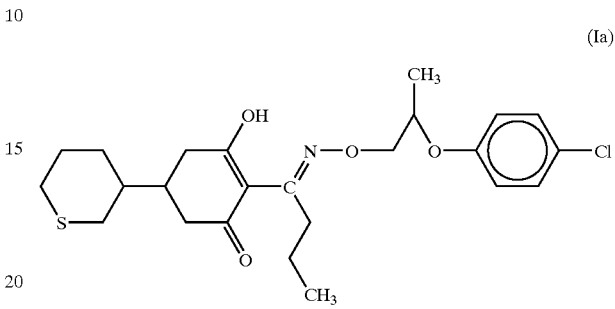

(Ia)

However, it is already known from EP-A 266 068 that herbicides from the substance class of the cyclohexenone oxime ethers tend to decompose. Particularly critical in this respect is the storage of corresponding crop protection formulations at elevated temperatures for a prolonged period of time. This also applies to the cyclohexenone oxime ethers of the formula (Ia) mentioned, including their metal salts.

In view of these problems, DE 195 10 887 describes storage-stable solid formulations which, in addition to a cyclohexenone oxime ether or a salt thereof, comprise certain water-soluble basic salts, in particular certain borates, phosphates, silicates, sulfites, citrates, acetates and carbonates. These are water-soluble compositions, preferably in the form of powders or granules.

For formulating certain cyclohexenone oxime ether metal salts, WO 97/20807 describes, in addition to solid formulations, also a large number of liquid formulations which are customarily employed in the area of crop protection. In this context, inert auxiliaries, such as oils, lower alcohols and strongly polar solvents, in particular water, and customary surfactants are mentioned as being substantially suitable for the formulations referred to in this publication. However, many of these auxiliaries cause, in a corresponding formulation, a rapid decomposition of the active compound.

It is an object of the present invention to provide stable liquid formulations of the cyclohexenone oxime ether of the formula (Ia) having good biological performance.

We have found that this object is achieved in the present invention by oil suspension concentrates of the corresponding lithium salt which are based on certain carboxylic esters and/or selected surfactants from the group of the sulfonates and the modified carboxylic acids.

Accordingly, the present invention provides, in particular, oil suspension concentrates comprising
(a1) 2-{1-[2-(4-chlorophenoxy)propoxyimino]butyl}-3-hydroxy-5-(tetrahydrothiopyran-3-yl)cyclohex-2-enone lithium salt of the formula (I)

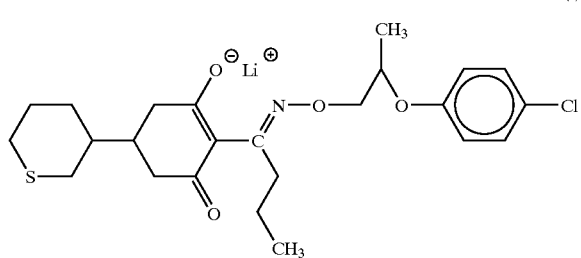

and at least one component selected from the group consisting of (b1) at least one mono- and/or dicarboxylic ester of the formula (IIa) or (IIb)

$$R^1\text{—CO—OR}^2 \quad (IIa)$$

$$R^3\text{—O—CO-A}^1\text{—CO—O—R}^4 \quad (IIb)$$

where $R^1$ is a straight-chain or branched saturated or unsaturated aliphatic radical having 6 to 30 carbons, $R^2$ is straight-chain or branched $C_1$–$C_8$-alkyl or $C_3$–$C_{10}$-cycloalkyl, $A^1$ is straight-chain or branched $C_2$–$C_6$-alkylene or $C_3$–$C_{10}$-cycloalkylene and $R^3$, $R^4$ independently of one another are a straight-chain or branched saturated or unsaturated aliphatic radical having 1 to 24 carbons;

(c1) at least one anionic surfactant of the formula III $$R^5\text{—SO}_3\text{-1/n M}^{(n+)} \quad (III)$$

where M is a mono- or divalent cation (n=1 or 2) and $R^5$ is a straight-chain or branched aliphatic or heteroaliphatic radical having 6 to 30 carbons or a ($C_6$–$C_{30}$-alkyl)aryl radical, and (c2) at least one nonionic surfactant of the formula (IV)

$$[R^6\text{—CO—(EO)}_x\text{-}]_y A^2 \quad (IV)$$

where $R^6$ is a straight-chain or branched saturated or unsaturated—optionally mono- or dihydroxylated—aliphatic radical having 8 to 30 carbons, the sum of all x being from zero to 100, y is from 1 to 7, $A^2$ is hydroxyl or $C_1$–$C_4$-alkyloxy if y is 1, or $A^2$ is derived from a $C_3$–$C_7$-polyol if y is from 2 to 7.

Accordingly, the present invention relates to liquid heterogeneous active compound-comprising formulations. They comprise solid active compound which is dispersed in an oily phase.

Oil suspension concentrates according to the invention are based on an active compound component (a) and a formulation component (F). If required, further additives may be present.

The proportion of the active component (a) in the oil suspension concentrate can be varied. It is typically in a range of from 1 to 70% by weight, preferably in a range of from 5 to 50 and in particular in a range of from 5 to 30% by weight.

In general, the stated quantities refer, unless indicated otherwise, to the total weight of the oil suspension concentrate. According to the invention, the term "substantially" generally denotes a percentage of at least 90%, preferably at least 95% and in particular at least 98%.

Terms such as alkyl, alkoxy, etc. include straight-chain and branched hydrocarbon groups, such as methyl, ethyl, n-propyl, isopropyl, n-butyl, isobutyl, sec-butyl, tert-butyl, n-pentyl, n-hexyl, n-octyl, 2-ethylhexyl, n-nonyl, isononyl, n-decyl, isodecyl, n-undecyl, isoundecyl, n-dodecyl, isododecyl, n-tridecyl, isotridecyl, stearyl and n-eicosyl having preferably—unless indicated otherwise—from 1 to 8, in particular from 1 to 6 and particularly preferably from 1 to 4 carbons in the case of short-chain radicals and from 6 to 30, in particular from 8 to 24 and particularly preferably from 12 to 24 carbons in the case of long-chain radicals.

The term "cycloalkyl" includes mono- and bicyclic saturated hydrocarbon groups such as cyclopropyl, cyclobutyl, cyclopentyl and especially cyclohexyl, etc., having preferably—unless indicated otherwise—from 3 to 10, in particular from 3 to 6 and particularly preferably 6 carbons, which groups may be mono-, di- or trisubstituted by $C_1$–$C_4$-alkyl. These statements apply analogously to "cycloalkylene" as corresponding divalent radicals, of which the cycloalkyl-1,2-ylenes are preferred.

The term "alkenyl" includes straight-chain and branched unsaturated hydrocarbon groups having preferably 1, 2 or 3 double bonds, such as ethenyl, prop-2-en-1-yl, oleyl, etc., having preferably—unless indicated otherwise—from 3 to 8, in particular from 2 to 6 and particularly preferably from 2 to 4 carbons in the case of short-chain radicals and from 6 to 30, in particular from 8 to 24 and particularly preferably from 12 to 24 carbons in the case of long-chain radicals.

The term "alkylene" includes straight-chain and branched divalent radicals, such as methylene, eth-1,1-ylene, eth-1,2-ylene, prop-1,1-ylene, prop-1,2-ylene, prop-1,3-ylene, prop-2,2-ylene, but-1,1-ylene, but-1,2-ylene, but-1,3-ylene, but-1,4-ylene, but-2,2-ylene, 2-methylprop-1,3-ylene, pent-1,1-ylene, pent-1,2-ylene, pent-1,3-ylene, pent-1,4-ylene, pent-1,5-ylene, pent-2,2-ylene, pent-2,3-ylene, pent-2,4-ylene, pent-3,3-ylene, 1-methylbut-1,4-ylene, 2-methylbut-1,4-ylene, etc., having preferably—unless indicated otherwise—from 2 to 18, in particular from 2 to 10 and particularly preferably from 2 to 6 carbons.

The lithium salt of the formula (I), 2-{1-[2-(4-chlorophenoxy)-propoxyimino]butyl}-3-hydroxy-5-(tetrahydrothiopyran-3-yl)-cyclohex-2-enone lithium salt, forms, as component (a1), at least part of the active compound component (a).

The way in which the compound of the formula (I) is presented here includes isomeric forms of this compound. In particular, geometric and stereoisomers, such as cis/trans isomers, enantiomers or diastereoisomers, and also tautomers which, in the present case, result in particular from the enolate structure, may be mentioned here. Accordingly, the compounds of the formula (I) can also be described as salt of a corresponding cyclohexane-1,3-dione derivative. In addition to the substantially pure isomers, the compound of the formula (I) embraces their isomer mixtures, for example mixtures of stereoisomers.

In addition to the lithium salt of the formula (I), the active compound component (a) may comprise one or more further crop protection agents.

In addition to 2-{1-[2-(4-chlorophenoxy)propoxyimino] butyl}-3-hydroxy-5-(tetrahydrothiopyran-3-yl)cyclohex-2-enone, other salts or derivatives thereof and also other cyclohexenone oxime ethers and salts thereof, agents for controlling pests or phytopathogenic fungi and/or bacteria are suitable, for example. In particular representatives of other herbicidal or growth-regulating groups of active compounds may be mentioned as further crop protection agents. These include, in particular as component (a2), crop protection agents selected from the following compounds:

bromobutide, dimepiperate, etobenzanid, propanil,
anilofos, mefenacet, 2,4-D and MCPB as metal salts, naproanilide,
bentazone, in particular as sodium salt,
pyrazolynate/pyrazolate, sulcotrione as metal salt, preferably from the 1st main group,
esprocarb, molinate, pyributicarb, thiobencarb/benthiocarb,
quinclorac,
butachlor, butenachlor, pretilachlor, thenylchlor,
cycloxydim, sethoxydim, in particular in the form of the sodium and/or lithium salts,
pendimethalin,
n-butyl (R)-2-[4-(4-cyano-2-fluorophenoxy)phenoxy]propionate, fenoxaprop-ethyl,
benzofenap, pyrazoxyfen,
dithiopyr,
sodium 2,6-bis[(4,6-dimethoxypyrimidin-2-yl)oxy]benzoate, methyl 2-[(4,6-dimethoxypyrimidin-2-yl)oxy]-6-[1-(methoxy-imino)ethyl]benzoate,
azimsulfuron, bensulfuron-methyl, cinosulfuron, cyclosulfamuron, ethoxysulfuron, imazosulfuron, pyrazosulfuron-ethyl, advantageously in the form of their metal salts,
dimethamethryn, simetryn/simetryne,
benfuresate,
cafenstrole,
cinmethylin, and
piperophos.

According to the invention, it is preferred to use the above active compounds, if they have acidic OH or NH functions, as agriculturally useful salts, in particular as metal salts with metal cations of the 1st and 2nd main group.

From among these further crop protection agents, it is possible to combine in an advantageous manner in particular salts of quinclorac having mono- (n=1) or divalent (n=2) metal cations $M^{(n+)}$, i.e. carboxylic acid salts of the formula (V)

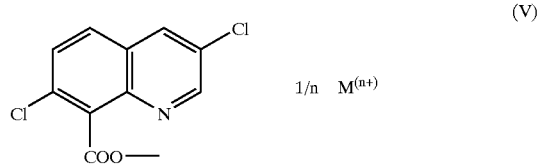

with the lithium salt of the formula (I).

According to one embodiment of the present invention, the active compound component (a) substantially comprises the lithium salt of the formula (I). This embodiment relates to oil suspension concentrates based on one herbicidally active compound (mono preparation).

According to a further embodiment of the present invention, the active compound (a) substantially comprises a combination of the lithium salt of the formula (I) and a carboxylic acid metal salt of the formula (V). This embodiment relates to oil suspension concentrates based on a herbicidal active compound combination (combination preparation).

The proportions of active compound in combination preparations can be varied within wide limits. Typically, the active compound component (a) comprises (a1) 5–95% by weight, preferably 10–70% by weight and in particular 20–50% by weight of the lithium salt of the formula (I) and (a2) 5–95% by weight, preferably 30–90% by weight and in particular 50–80% by weight of a carboxylic acid metal salt of the formula (V) and (a3) if appropriate, up to 90% by weight, preferably up to 60% by weight and in particular up to 30% by weight of a further, preferably herbicidal, crop protection agent, where the stated quantities are in each case based on the total weight of the active compound component (a) and the sum of components (a1), (a2) and (a3) is, according to a particular embodiment, 100% by weight.

According to another aspect, the active compound component (a) comprises relatively larger proportions by weight of carboxylic acid metal salts of the formula (V) than of the lithium salt of the formula (I). Typically, this ratio by weight of (I) to (V) is in a range of from 1:1.1 to 1:4, preferably from 1:1.5 to 1:3 and in particular from 1:2 to 1:2.75.

The purpose of the formulation component (F) is to form an oil suspension concentrate based on the lithium salt of the formula (I). Furthermore, parts of the formulation component may have adjuvant action, in particular activity-enhancing action.

At least part of the total amount of the lithium salt of the formula (I) present in the oil SC is present as a solid. Another, generally smaller, part of the lithium salt of the formula (I) may be the salt in the formulation component (F). The proportion of dissolved lithium salt of the formula (I), based on the total amount in the oil SC, is advantageously less than 1% by weight, preferably less than 0.5% by weight and in particular less than 0.3% by weight.

In the formulation component (F), the solid fraction forms a heterogeneous phase (suspension). The solid is advantageously present in dispersed form. The formation of stable dispersions is preferred.

Solid active compound is generally present in particulate form. The main particle size of the active compound particles is advantageously less than 10 μm and in particular less than 5 μm. Advantageous particle sizes are in a range of from 0.1 μm to 10 μm, and in particular from 0.5 μm to 5 μm. According to a further aspect, advantageous cumulative sum distributions for the particle sizes can be described as distributions where at least 50% of the particles have a particle size of less than 100 μm, preferably less than 50 μm and in particular less than 10 μm. Oil suspension concentrates having cumulative sum distributions of particle sizes where at least 90% of the active compound particles have a particle size of less than 10 μm and in particular less than 5 μm are particularly preferred. The above statements on the particle sizes refer to measurements at room temperature using the Cilas granulometer 715 from Cilas, Marcoussis, France, measuring samples saturated with solid which, if required, are diluted with the fluid phase of the oil SC according to the invention.

If the active compound component (a) comprises one or more further crop protection agents, these can be distributed in the formulation component (F) in principle in any form. Thus, further crop protection agents can, independently of one another, be present at least partially as a solid or in dissolved form. Advantageously, further crop protection agents contained in the active compound component (a), too, form a heterogeneous phase. Particular embodiments of this case result from what was said above about the lithium salt of the formula (I), which applies analogously to further crop protection agents and in particular to carboxylic acid metal salts of the formula (V).

Thus, one embodiment of the present invention relates to oil suspension concentrates of the lithium salt of the formula (I) having the proportions of active compound, proportions of solid and/or particle sizes described above. These include, in particular, oil suspension concentrates having a content of lithium salt of the formula (I) of from 10 to 30% by weight, a proportion of solid, based on the total amount of lithium salt, of at least 99% by weight, a mean particle size of from 1 to 3 μm and a cumulative sum distribution of particle sizes where typically at least 60% of the particles have a particle size of less than 2 μm.

According to a further embodiment, the present invention relates to oil suspension concentrates of the lithium salt of the formula (I) and at least one carboxylic acid metal salt of the formula (V) having the proportions of active compounds, proportions of solids and/or particle sizes described above.

The proportion of the formulation component (F) is generally from to 99% by weight, preferably from 50 to 95% by weight, and in particular from 70 to 95% by weight. The formulation component (F) is usually composed of a plurality of components. These components include auxiliaries whose function is primarily related to aspects of formulation. In this sense, the components can also be referred to as auxiliary components. However, this term includes further functions and actions of these components, for example active compound-stabilizing and, in particular, activity-enhancing effects.

The formulation component (F) includes, in particular, at least one fluid component (b) and at least one surfactant component (c).

The proportion of the fluid component (b), based on the total weight of the oil suspension concentrate, is generally from 10 to 90% by weight, preferably from 30 to 80% by weight and in particular from 40 to 70% by weight.

Component (b) serves primarily as solvent for soluble components or as diluent for insoluble components of the oil suspension concentrate.

At least part of the component (b) is formed by one or more oils. According to the invention, the term "oil" denotes a substance which is liquid and virtually insoluble in water under the use conditions of the oil suspension concentrate. For the purpose of the invention, substances are water-insoluble in particular when, to dissolve one part of substance, at least 1000–10000 parts and preferably at least 10 000 parts of water are required.

Suitable in principle are, for example, mineral oils, synthetic oils and also vegetable and animal oils.

These include in particular aprotic solvents, such as mineral oil fractions of medium to high boiling point, for example kerosene and diesel fuel, furthermore coal tar oils, hydrocarbons, paraffin oils, unhydrogenated, hydrogenated or partially hydrogenated aromatic or alkylaromatic compounds from the benzene or naphthalene series, aliphatic or aromatic carboxylic or dicarboxylic esters, in particular the esters of the formulae (IIa) and (IIb), fats and oils of vegetable or animal origin, such as mono-, di- and triglycerides, pure or as a mixture, for example in the form of oily extracts of natural products, for example olive oil, soybean oil, sunflower oil, castor oil, sesame oil, corn oil, groundnut oil, rapeseed oil, linseed oil, almond oil, safflower oil, and their raffinates, for example hydrogenated or partially hydrogenated products thereof and/or their esters, in particular methyl and ethyl esters.

The oil proportion of the total weight of the oil suspension concentrate is generally from 10 to 90% by weight, preferably from 30 to 80% by weight and in particular from 40 to 70% by weight.

According to a particular embodiment, component (b) of the oil suspension concentrates according to the invention comprises at least the abovementioned component (b1).

According to a further particular embodiment, the abovementioned component (b1) is, as part of a further formulation (stand alone product), mixed with the oil suspension concentrates according to the invention at an expedient point of time, generally shortly before the application.

According to the invention, the mono- and dicarboxylic esters of the formula (IIa) and (IIb), respectively, belong to the oils. They have long-chain aliphatic radicals which can be derived from fatty acids or fatty alcohols. This applies to the meaning of the radicals $R^3$ and $R^4$ in the dicarboxylic esters of the formula (IIb) and in particular to the monocarboxylic esters of the formula (IIa) and here specifically to the meaning of the radical $R^1$.

The radicals can be derived, for example, from fatty acids such as tridecanoic acid, lauric acid, elaeostearic acid, undecanoic acid, capric acid, erucic acid, pelargonic acid, caprylic acid, enanthic acid, caproic acid, isostearic acid, oleic acid, palmitoleic acid, linolic acid, linoleic acid, arachidonic acid, clupanodonic acid and docosahexaenoic acid.

Accordingly, $R^1$ is expediently a straight-chain or branched—in particular branched once—saturated or—up to hexa- and in particular mono-—unsaturated aliphatic radical having 6 to 30 and preferably 8 to 24 carbons. These include in particular the corresponding alkyl and alkenyl radicals. A preferred alkyl radical is dodecanyl. A preferred alkenyl radical is octadec-9-enyl, in particular cis-octadec-9-enyl (oleyl).

If the radical $R^1$ is a relatively long-chain radical, the radical $R^2$ is generally derived from relatively short-chain alcohols. Thus, $R^2$ is expediently straight-chain or branched alkyl—in particular alkyl which is branched once or twice—having 1 to 8, preferably 1 to 6 and in particular 1 to 4 carbons, or cycloalkyl having preferably 6 carbons. Preferred alkyl radicals are methyl, ethyl, isopropyl, butyl, 2-ethylhexyl and also n- and isooctyl. Particularly preferred are methyl, ethyl and butyl, and among these especially methyl. A preferred cycloalkyl radical is cyclohexanyl.

It is possible to use, for example, the following monocarboxylic esters of the formula (IIa) alone, or in combination with one another and also with dicarboxylic esters of the formula (IIb): oleic acid esters, in particular methyl oleate and ethyl oleate, lauric acid esters, in particular 2-ethylhexyl laurate, octyl laurate and isopropyl laurate, isopropyl myristate, palmitic acid esters, in particular 2-ethylhexylpalmitate and isopropyl palmitate, stearic acid esters, in particular n-butyl stearate, and 2-ethylhexyl 2-ethylhexanoate. Particular emphasis is given to the oleic acid esters, in particular methyl oleate.

The radical $A^1$ is a divalent radical which links two carboxyl carbons. Thus, $A^1$ is expediently straight-chain or branched alkylene—in particular alkylene which is branched once—having 2 to 6 and preferably 2 to 4 carbons or is cycloalkylene, in particular cyclohexylene. Preferred alkylene radicals are eth-1,2-ylene, prop-1,3-ylene and especially but-1,4-ylene. A preferred cycloalkylene radical is cyclohex-1,2-ylene.

The radicals $R^3$ and $R^4$ may differ. For practical reasons, use is made in particular of dicarboxylic esters in which $R^3$ and $R^4$ have the same meaning. In principle, $R^3$ and $R^4$ may be derived from short- and long-chain alcohols. Expediently, $R^3$ and $R^4$ independently of one another represent a straight-chain or branched aliphatic radical—in particular a radical which is branched once—which is saturated or—in particular mono- or di- —unsaturated and has 1 to 24, preferably 1 to 12, carbons. These include in particular the corresponding alkyl and alkenyl radicals. Preferred alkyl radicals are methyl and ethyl, but also octyl and nonyl, in particular isononyl.

It is possible to use, for example, the following dicarboxylic esters of the formula (IIb) alone, or in combination with one another and also with monocarboxylic esters of the formula (IIa): adipic acid esters, in particular dimethyl adipate, di-n-butyl adipate, di-n-octyl adipate, diisooctyl adipate, also referred to as bis(2-ethylhexyl) adipate, di-n-nonyl adipate, diisononyl adipate and ditridecyl adipate; succinic acid esters, in particular di-n-octyl succinate and diisooctyl succinate, and diisononyl cyclohexane-1,2-dicarboxylate. Particular emphasis is given to dimethyl adipate, bis(2-ethylhexyl) adipate and diisononyl adipate.

The proportion of mono- and dicarboxylic esters of the formulae (IIa) and (IIb), respectively, is, when these compounds are present, generally from 5 to 70% by weight, preferably from 15 to 60% by weight and in particular from 20 to 50% by weight, based on the total weight of the oil suspension concentrate.

According to one embodiment, the present invention relates to oil suspension concentrates having a component (b) which is essentially formed from at least one mono- and/or dicarboxylic ester of the formulae (IIa) and (IIb), respectively (component (b1)).

According to an alternative embodiment, the component (b) does not comprise a mono- and/or dicarboxylic ester of the formulae (IIa) and (IIb), respectively, but instead at least one further oil as component (b2). This component (b2) can be selected, in particular, from the oils and aprotic solvents mentioned above. In particular, (b2) at least one $C_8$- to $C_{30}$-hydrocarbon and the n- or isoalkane series or a mixture thereof, and aromatic or cycloaliphatic $C_7$— to $C_{18}$-hydrocarbon compounds, or mixtures thereof, may be mentioned here.

Examples of $C_8$- to $C_{30}$-hydrocarbons of the n- or isoalkane series are n- and isooctane, -decane, -hexadecane, -octadecane, -eicosane, and preferably hydrocarbon mixtures, such as paraffin oil (which, when technical grade, may comprise about 5% of aromatic compounds) and a $C_{18}$–$C_{24}$ mixture which is commercially available under the name Spraytex Öl from Texaco.

The aromatic or cycloaliphatic $C_7$- to $C_{18}$-hydrocarbon compounds include, in particular, aromatic or cycloaliphatic solvents from the group of the alkylaromatic compounds. These compounds can be unhydrogenated, partially hydrogenated or fully hydrogenated. Such solvents of component (b2) include, in particular, mono-, di- or trialkylbenzenes, mono-, di-, trialkyl-substituted tetralines and/or mono-, di-, tri- or tetraalkyl-substituted naphthalenes (alkyl is preferably $C_1$–$C_6$-alkyl). Examples of such solvents are toluene, o-, m-, p-xylene, ethylbenzene, isopropylbenzene, tert-butylbenzene and mixtures, such as the products sold under the names Shellsol and Solvesso from Exxon, for example Solvesso 100, 150 and 200.

The component (b2) is preferably selected from the group which contains at least one unhydrogenated, fully hydrogenated or partially hydrogenated alkylaromatic compound from the benzene or naphthalene series, especially the products sold under the trade names Shellsol and Solvesso by Exxon, for example Solvesso 100, 150 and 200. Accordingly, component (b2) can substantially be formed from said alkylaromatic compounds. However, it may additionally comprise $C_8$- to $C_{30}$-hydrocarbons of the n- or isoalkane series which, in many cases, are co-introduced, for practical reasons.

In the oil suspension concentrates according to the invention, the proportion of $C_8$- to $C_{30}$-hydrocarbons of the n- or isoalkane series should advantageously be lower than the proportion of a possible component (b1) or than the proportion of the component (b2). The ratio by weight of the proportion of $C_8$- to $C_{30}$-hydrocarbons of the n- or isoalkane series to the proportion of active compound is preferably less than 3:1, with preference less than 1.5:1 and in particular less than 0.5:1.

In a further embodiment, the present invention also relates to oil suspension concentrates having a component (b) which, in addition to at least one mono- and/or dicarboxylic ester of the formulae (IIa) and (IIb), respectively, comprises at least one further oil as component (b2).

In the context of this embodiment, the proportion of mono- and dicarboxylic esters of the formulae (IIa) and (IIb), respectively, is generally from 5 to 70% by weight and preferably from 15 to 60% by weight and the proportion of further oils (component (b2)) is generally from 5 to 60% by weight and preferably from 10 to 45% by weight.

Advantageously, oil suspension concentrates according to the invention comprise substantially no or only very small proportions of $C_1$–$C_8$-monoalcohols, such as methanol, ethanol, propanol, isopropanol, butanol, isobutanol, tert-butanol, cyclohexanol and 2-ethylhexanol, $C_1$–$C_8$-ketones, such as cyclohexanone, and strongly polar solvents, such as water.

Based on the total weight of the oil suspension concentrate, the proportion of said alcohols and ketones is preferably less than 10% by weight and in particular less than 5% by weight.

The water content of the oil suspension concentrates according to the invention, based on the total weight of the formulations, is preferably less than 1% by weight and in particular less than 0.5% by weight. Very particular preference is given to oil suspension concentrates whose water content is in a range of from 0.1 to 0.5% by weight and in particular in a range of from 0.05 to 0.25% by weight.

The proportion of the surfactant component (c), based on the total weight of the oil suspension concentrate, is generally from 10 to 60% by weight, preferably from 15 to 40% by weight and in particular from 20 to 30% by weight.

Component (c) serves in particular as dispersant and/or emulsifier, in particular for dispersing the solids fraction in the oil suspension concentrate or for emulsifying the oil phase of an oil suspension concentrate added in water. Furthermore, parts of the component (c) may serve as wetting agent.

At least part of the component (c) is formed by one or more surfactants. Here, the term "surfactant" denotes interface-active or surface-active agents.

Suitable in principle are anionic, cationic and amphoteric surfactants, including polymer surfactants and surfactants having heteroatoms in the hydrophobic group.

The anionic surfactants include, for example, carboxylates, in particular alkali metal, alkaline earth metal and ammonium salts of fatty acids, for example potassium stearate, which are usually also referred to as soaps; acyl glutamates; sarcosinates, for example sodium lauroyl sarcosinate; taurates; methylcelluloses; alkyl phosphates, in particular alkyl mono- and diphosphates; sulfates, in particular alkyl sulfates and alkyl ether sulfates; sulfonates, in particular sulfonates of the formula (III), further alkyl- and alkylaryl sulfonates, in particular alkali metal, alkaline earth metal and ammonium salts of arylsulfonic acids and also alkyl-substituted arylsulfonic acids, alkylbenzenesulfonic acids, such as, for example, ligno- and phenolsulfonic acid, naphthalene- and dibutylnaphthalenesulfonic acids, or dodecylbenzene sulfonates, alkylnaphthalene sulfonates, alkylmethyl ester sulfonates, condensates of sulfonated naphthalene and derivatives thereof with formaldehyde, condensates of naphthalenesulfonic acids, phenol- and phenolsulfonic acids with formaldehyde or with formaldehyde and urea, mono- or dialkylsuccinic acid ester sulfonates; and also protein hydrolysates and lignosulfite waste liquors. The sulfonic acids mentioned above are advantageously employed in the form of their neutral or, if appropriate, basic salts.

The cationic surfactants include, for example, quaternary ammonium compounds, in particular alkyltrimethylammonium and dialkyldimethylammonium halides and alkylsulfates and also pyridine and imidazolidine derivatives, in particular alkylpyridinium halides.

The nonionic surfactants include, for example, the compounds of the formula (Iv), further alkoxylates and in particular ethoxylates and also nonionic surfactants, in particular fatty alcohol polyoxyethylene esters, for example lauryl alcohol polyoxyethylene ether acetate, alkyl polyoxyethylene and polyoxypropylene ethers, for example of isotridecyl alcohol, and fatty alcohol polyoxyethylene ethers, alkylaryl alcohol polyoxyethylene ethers, for example octylphenol polyoxyethylene ether, alkoxylated animal and/or vegetable fats and/or oils, for example corn oil ethoxylates, castor oil ethoxylates, tallow fat ethoxylates, glycerol esters, such as, for example, glycerol monostearate, fatty alcohol alkoxylates and oxoalcohol alkoxylates, in particular of the type $RO-(R_9O)_x(R_{10}O)_yR_{11}$ where $R_9$ and $R_{10}$ independently of one another $=C_2H_4$, $C_3H_6$, $C_4H_8$ and $R_{11}=H$, or $C_1-C_{12}$-alkyl, $R=C_3-C_{30}$-alkyl or $C_6-C_{30}$-alkenyl, x and y independently of one another are 0 to 50, it not being possible for both to be 0, such as isotridecyl alcohol and oleyl alcohol polyoxyethylene ether, alkylphenol alkoxylates, such as, for example, ethoxylated isooctyl, octyl or nonylphenol, tributylphenol polyoxyethylene ether, fatty amine alkoxylates, fatty acid amide alkoxylates and fatty acid diethanolamide alkoxylates, in particular their ethoxylates, sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylgluconamides, alkylmethyl sulfoxides, alkyldimethylphosphine oxides, such as, for example, tetradecyldimethylphosphine oxide.

The amphoteric surfactants include, for example, sulfobetaines, carboxybetaines and alkyldimethylamine oxides, for example tetradecyldimethylamine oxide.

Polymeric surfactants include, for example, di-, tri- and multi-block copolymers of the type $(AB)_x$, ABA and BAB, for example polyethylene oxide block polypropylene oxide block polyethylene oxide, polystyrene block polyethylene oxide, and AB-comb polymers, for example polymethacrylate comb polyethylene oxide.

Other surfactants which may be mentioned here by way of example are perfluoro surfactants, silicone surfactants, phospholipids, such as, for example, lecithin or chemically modified lecithins, amino acid surfactants, for example N-lauroylglutamate, and surface-active homo- and copolymers, for example polyvinylpyrrolidone, polyacrylic acids in the form of their salts, polyvinyl alcohol, polypropylene oxide, polyethylene oxide, maleic anhydride/isobutene copolymers and vinylpyrrolidone/vinyl acetate copolymers.

Unless specified otherwise, the alkyl chains of the surfactants listed above are linear or branched radicals of usually from 8 to 20 carbons.

The component (c) of oil suspension concentrates according to the invention preferably comprises at least one of the surfactant components (c1) and (c2) listed above.

The surfactant component (c1) is formed by at least one anionic surfactant of the formula (III). These are certain sulfonates which include, in particular, alkanesulfonates and sulfosuccinates, so that $R^5$ is expediently an aliphatic or heteroaliphatic radical which is straight-chain or branched—in articular once or twice—and has 6 to 30, preferably at least 8 and in particular 12 to 24 carbons. For alkanesulfonates, $R^5$ may be derived, in particular, from fatty alkyl radicals, for example corresponding to the fatty acids mentioned above. Certain heteroaliphatic radicals are interrupted by one or two ester groupings —OC(O)—. In this context, $R^1$ is in particular succin-2-ylate, including mono- and diesters, and a fatty acid ester attached in the α-position.

Sulfosuccinates are preferred anionic surfactants of the formula III. Here, $R^5$ is a radical —CH(C(O)—O—$R^7$)CH$_2$—C(O)—O—$R^8$ in which $R^7$, $R^8$ independently of one another may have the meanings given for $R^3$ and $R^4$ and are in particular alkyl radicals having 1 to 12 and preferably 5 to 8 carbons. A preferred alkyl radical is octyl, in particular isooctyl.

The negative charge of ionic surfactants requires countercations, so that M is a mono- or divalent cation. In principle, any inorganic or organic cation suitable for use in agriculture is suitable. Preference is given to the cations of metals such as lithium, sodium, calcium, potassium, magnesium, zinc, manganese, and lithium, sodium and calcium are particularly preferred.

A preferred sulfosuccinate is dioctylsuccinate, for example the sodium salt.

The anionic surfactants of the formula III also include alkylarylsulfonates, so that $R^5$ is expediently also an alkyl-substituted aryl radical. The aryl radical may be mono- or polysubstituted, in the case of polysubstitution in particular disubstituted or trisubstituted, by identical or different alkyl radicals, where two substituents may be located at the same position. In general, the alkyl radicals have from 6 to 30, preferably from 10 to 24 and in particular from 8 to 12 carbons. Independently of one another, they can be straight-chain or branched—in particular 1-, 2-, 3- or 4-times. From among the straight-chain radicals, decanyl, undecanyl, dodecanyl, tridecanyl and tetradecanyl may be mentioned, for example, and from among the branched radicals, for example, tetrapropylene. A preferred aryl radical is phenyl.

A preferred alkylarylsulfonate is dodecylphenylsulfonate, for example the sodium, lithium or calcium salt.

If present, the proportion of anionic surfactant of the formula III, based on the total weight of the oil suspension concentrate, is generally from 1 to 40% by weight, preferably from 7.5 to 30% by weight and in particular from 10 to 30% by weight.

The surfactant component (c2) is formed by at least one nonionic surfactant of the formula IV. These are unethoxylated or ethoxylated carboxylic acids and esters of mono- or polyhydric alcohols (polyols).

The radical $R^6$ is, in particular, derived from fatty acid radicals, for example those mentioned above, so that $R^6$ is expediently a straight-chain or branched aliphatic radical—in particular a radical that is branched once or twice—which is saturated or—in particular mono-, di- or tri-—unsaturated, which may be mono- or dihydroxylated and has 8 to 30, preferably 12 to 24, and in particular 10 to 24 carbons. These include in particular palmityl, stearyl, arachidyl, hexadecenyl, oleyl, linolyl, linolenyl, ricinoleyl, eicosanyl and also mono- and dihydroxystearyl, from among which ricinoleyl and oleyl are preferred.

If the nonionic surfactants of the formula IV are ethoxylated, the sum of all x is the mean ethoxylation number, generally from 3 to 100 and in particular from 5 to 50.

If $A^2$ is hydroxyl, y=1 and the mean ethoxylation number is advantageously from 5 to 50 and preferably from 15 to 40. In this context, in particular the corresponding castor oil and oleic acid polyethoxylates may be mentioned.

If $A^2$ is straight-chain or branched alkyloxy having 1 to 4 and preferably 1 or 2 carbons, then y=1 and the mean ethoxylation number is from 3 to 100 and preferably from 20 to 50.

If $A^2$ is derived from a polyol having 3 to 7 and in particular 6 carbons, the value of y is from 2 to 7 and preferably from 3 to 6. Here, y hydroxy hydrogen atoms of the radical $A^2$ are in each case replaced by a radical $R^6$—CO—$(EO)_x$—, where a plurality of radicals $R^6$ and a plurality of indices x may be identical or different. Preferably, a plurality of radicals $R^6$ are identical, whereas the indices x may be different and generally follow a Gaussian distribution. In particular, $A^2$ is derived from a sugar alcohol, such as sorbitol or glycerol. A preferred meaning of $A^2$ is sorbitol. When the radical is ethoxylated, the mean ethoxylation number is from 5 to 50 and preferably from 15 to 40. In this context, in particular the corresponding sorbitol polyethoxy oleates and stearates may be mentioned.

If present, the proportion of nonionic surfactants of the formula IV, based on the total weight of the oil suspension concentrate, is generally from 1 to 40% by weight, preferably from 2.5 to 25% by weight and in particular from 5 to 15% by weight.

In one embodiment, the present invention relates to oil suspension concentrates having a component (c) which is substantially formed by a surfactant component (c1) or a surfactant component (c2).

In a further embodiment, the present invention relates to oil suspension concentrates having a component (c) which is substantially formed by a mixture of the surfactant components (c1) and (c2). In the context of this embodiment, the proportion of surfactant component (c1) is generally from 1 to 40% by weight and preferably from 7.5 to 30% by weight and the proportion of surfactant component (c2) is generally from 1 to 20% by weight and preferably from 5 to 10% by weight, the proportions in question being based on the total weight of the oil suspension concentrate.

In a further embodiment, the present invention relates to oil suspension concentrates having a component (c) which, additionally to surfactant component (c1) and/or surfactant component (c2), comprises further surfactants chosen, in particular, from those described above.

Here, the proportion of further surfactants in the oil suspension concentrates according to the invention should advantageously be lower than the proportion of surfactants of the formula (III) and/or (IV). The weight ratio of the proportion of further surfactants to the proportion of active compound is preferably less than 1.5:1, with preference less than 1:1 and in particular less than 0.5:1.

The proportion of the component essentially consisting of component (b1), (c1) and/or (c2) is generally greater than 10% by weight, preferably greater than 20% by weight and in particular greater than 25% by weight. This total proportion is advantageously in a range of from 30 to 90% by weight, preferably from 30 to 80% by weight and in particular from 35 to 75% by weight.

Preference according to the invention is given to oil suspension concentrates having a formulation component (F) which is, at least in part, based on a fluid component (b1) in combination with a surfactant component (c1) and/or (c2). Based on the total weight of the oil suspension concentrate, the proportion of the fluid component (b1) together with the surfactant component (c1) and/or (c2) is advantageously from 10 to 90% by weight, preferably from 15 to 85% by weight and in particular from 20 to 70% by weight. Particular embodiments of these oil suspension concentrates result in accordance with the embodiments described above with respect to the components (b1), (c1) and (c2).

Thus, according to a particularly preferred embodiment, the present invention relates to oil suspension concentrates based on components (b1), (c1) and (c2). These oil suspension concentrates may in particular also comprise a component (b2).

If present, the proportion of further auxiliaries as component (d), based on the total weight of the oil suspension concentrate, is generally up to 15% by weight and preferably up to 10% by weight.

The component (d) may have multifarious functions. Suitable auxiliaries are chosen according to what is required, usually by the person skilled in the art. Particular mention may be made of stabilizers.

Preferred stabilizers are lithium salts, which can be used as component (d1). These include lithium salts of inorganic or organic acids, in particular lithium hydroxide, lithium carbonate, lithium chloride and lithium carboxylates and also sulfonates of organic carboxylic acids and sulfonic acids, in particular of the sulfonic acids of the formula (III). Such lithium salts may be dissolved in the oil suspension concentrate or—at least in part—be present as a solid, for example in particulate and in particular in disperse form.

If present, the proportion of the component (d1), based on the total amount of active compound in lithium salt form, is advantageously from 1 to 30 mol % and preferably from 3 to 20 mol %.

The stabilizers used as component (d2) can also be antisettling agents. These serve in particular for the rheologic stabilization of the oil suspension concentrates according to the invention. In some cases, it is possible to improve the thixotropic properties of the formulation. Their purpose is, in particular, to prevent the settling of solids and/or agglomeration effects in the oil suspension concentrates. It is desirable to reduce the formation of serum and/or the sedimentation of solids.

Suitable antisettling agents can be found, for example, among the thickeners. These are in particular substances capable of forming a gel-like structure, thus increasing the viscosity of the fluid phase of the oil suspension concentrates according to the invention. These include, for example, organic polymers and also inorganic substances, in particular finely divided mineral substances such as bentonite, talcite or hectorite. Basic mineral systems, for example talcites, which, if appropriate, are converted from the carbonate form into the hydroxide form by calcination, have been found to be particularly suitable.

If present, the proportion of the component (d2), based on the total weight of the oil suspension concentrate, is advantageously up to 15% by weight and preferably from 1 to 10% by weight.

The stabilizers also include water-binding agents, which can be used as component (d3). In this context, mention may be made in particular of alkylene boron salts, in particular anhydrous, calcined or dewatered boron salt of the borax type.

If present, the proportion of the component (d3), based on the total weight of the oil suspension concentrate, is advantageously up to 15% by weight and preferably from 2 to 10% by weight. In addition to the active compound component (a) and the formulation component (F), the oil suspension concentrates according to the invention may comprise further additives. Of interest are, for example, the miscibility with mineral salt solutions used to redress nutrient and trace element deficiencies. It is also possible to use nonphytotoxic oils and oil concentrates and also antidrift agents. Suitable are furthermore antifoams, in particular those of the silicone type, for example silicone SL sold by Wacker, which can be added in any amount of from 0.1 to 10 g, preferably from 1 to 2 g, per liter.

The oil suspension concentrates according to the invention can be prepared in a manner known per se. To this end, at least parts of the components are added together. Here, it has to be noted that products, in particular commercial products, can be used whose ingredients may contribute to different components. A certain surfactant, for example, may be dissolved in an aprotic solvent, so that this product contributes both to component (b) and to component (c). Furthermore, small proportions of undesirable substances, such as water or lower alcohols or ketones, may be introduced with commercial products. Accordingly, the products to be incorporated into the oil SCs according to the invention are advantageously selected using the criterion of a relatively low content of water and/or lower alcohols or ketones. To obtain a mixture, in particular in the form of a suspension, the added products generally have to be ground intensively.

The grinding medium used can be glass grinding medium or other mineral or metallic grinding media, generally of a size of 0.1–30 mm, and in particular of 0.6–2 mm. The mixture is generally comminuted until the desired particle size has been achieved.

In general, grinding can be carried out with recirculation, i.e. continuous pumping of the oil SC in a circle, or in passage operation, i.e. complete and repeated pumping-through or processing of an oil SC batch.

Grinding can be carried out using customary ball, bead or agitated mills, for example in a Dyno-mill (from Bachofen), using batch sizes of, for example, from 0.5 to 1 liter in passage operation. After several—in particular 4 to 6—passages (the slurry being pumped through the mill using a peristaltic pump), mean particle sizes of from 0.5 to 10 μm are achieved, according to microscopic evaluation.

It is then possible to incorporate further auxiliaries, for example by homogenization using suitable apparatus such as ground-glass or magnetic stirrers.

There are a plurality of possible preparation variants, for example direct grinding or blending from an oil suspension concentrate preconcentrate.

For direct grinding, the major part of component (b) is initially charged together with component (c) and the active compound component (a) is added as a solid. The formulation batch is then made up with the remaining amount of component (b). The batch is then ground as described above. Any component (d) to be added may be added at any time. Preference is given to also grinding the stabilizers, in particular inorganic stabilizers. Grinding may take place together with the active compound. However, the stabilizers may also be ground separately, for example as master batches, in which case usually a higher concentration is processed which is then added to the oil suspension concentrate.

For blending from the oil suspension concentrate preconcentrate, the active compound component (a) is initially, together with part of component (b), ground in the manner described above to give a preconcentrate. The preconcentrate is then initially charged, component (c) is added and the desired active compound content is established by adding further component (b). Here, too, component (d), if present, can be admixed at any time. Again, it is preferred to add stabilizers during grinding.

When preparing the oil suspension concentrates, the lithium salt of the formula (I) can be employed as a solid.

Processes which are suitable in principle for preparing 2-{1-[2-(4-chlorophenoxy)propoxyimino]butyl}-3-hydroxy-5-(tetrahydrothiopyran-3-yl)cyclohex-2-enone lithium salt of the formula (I) are illustrated, for example, in WO 97/20807. These include the reaction of 2-{1-[2-(4-chlorophenoxy)propoxyimino]-butyl}-3-hydroxy-(5-tetrahydrothiopyran-3-yl)cyclohex-2-enone of the formula (Ia)

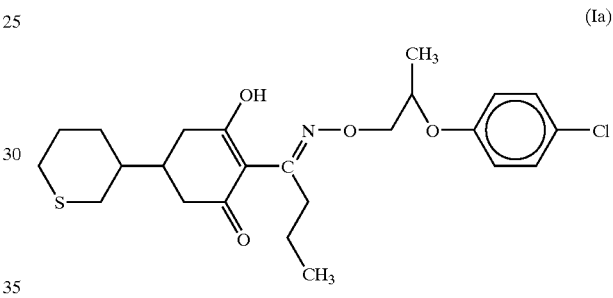

(Ia)

with a basic lithium salt and the isolation of the compound of the formula (I). Suitable basic lithium salts are, for example, the corresponding hydrides, hydroxides, alkoxides or carbonates. The lithium salt of the formula (I) can furthermore be prepared from the corresponding cyclohexenone oxime ether sodium salt by sodium/lithium exchange.

The compound of the formula (Ia) is preferably reacted with lithium hydroxide in a solvent mixture comprising methanol and at least one aromatic hydrocarbon, and prior to the isolation of the compound of the formula (I), at least part of the solvent is removed. Suitable aromatic hydrocarbons include, in particular, solvents of the benzene series, such as alkyl-substituted benzenes, for example toluene and xylene. Toluene is particularly suitable. Thus, preferably, a solution of the compound (Ia) in toluene is used. The concentration of the compound of the formula (Ia) is preferably from 5 to 40% by weight, with preference from 10 to 30% by weight and in particular about 20% by weight, based on the total weight of the solution to be employed. Lithium hydroxide (LiOH) can be used, for example, in anhydrous form or as a hydrate, in particular the monohydrate. Preference is given to using a solution of LiOH based on methanol which may, however, additionally contain other solvents. Preference is given to methanolic LiOH solutions which, in addition to possible further solvents, comprise at least 70% by weight, preferably at least 80% by weight and in particular at least 85% by weight of methanol, based on the total amount of solvent in the LiOH solution to be used. A methanolic LiOH solution expediently comprises from 1 to 7% by weight, preferably from 2 to 6% by weight and in particular about 5% by weight of LiOH. The stated amounts are based on the total weight of the solution employed, prior to the addition. To ensure complete conversion, the lithium hydroxide solution is usually employed in a molar excess. Preference is given to using a molar excess of from 0.5 to 10%, based on the cyclohexenone oxime ether (Ia) used as starting material. However, it may also be expedient to react lithium hydroxide in a molar ratio of 1:1 with the cyclohexenone oxime ether (Ia). In this case, for example, the addition of LiOH, in particular as lithium hydroxide solution, may be monitored with a suitable pH electrode and solution may be metered in until the equivalence point is reached. The respective reaction partners are usually metered in over a period of from 10 minutes to 360 minutes, preferably from 10 minutes to 120 minutes, in particular about 30 minutes. The reaction is usually carried out at temperatures of from −20° C. to 60° C., preferably 0–40° C., particularly preferably 20–30° C. Prior to the isolation of the cyclohexenone oxime ether solvent (I), at least part of the solvent mixture, in particular methanol, is removed from the solvent mixture. This generally takes place together with other components of the solvent mixture, in particular as a methanol/toluene/water mixture. The removal is preferably carried out by distillation, usually at temperatures between 20 and 70° C., preferably at 30–60° C. and particularly preferably at 40–50° C. The distillation can be carried out under atmospheric pressure or, preferably, under reduced pressure. A suspension is formed. Accordingly, it may be expedient to remove such an amount of solvent that the compound of the formula (I) substantially precipitates out completely. According to a particular aspect, methanol is removed from the reaction mixture substantially completely. The cyclohexenone oxime ether lithium salt (I) is usually isolated by subjecting the resulting suspension to a solid/liquid separation. Preference is given to filtration, in particular pressure filtration, belt filtration, vacuum filtration, centrifugation and the like. It is generally expedient to purify the solid that is separated off, in particular in the form of a filter cake. To this end, the solid may be washed with a suitable solvent, in particular with toluene. In general, it is also expedient to dry the solid that has separated off, in particular the filter cake. A particular form of the product obtainable by this process has a content of (I) of at least 96% by weight, preferably at least 97% by weight and in particular at least 98% by weight, based on the total weight of the product obtained.

These processes do not only permit the process product to be isolated in a comparatively efficient manner; the cyclohexenone oxime ether Li salts (I) preparable by this process surprisingly also form comparatively stable oil SC formulations. This is of importance in particular for a use as rice herbicide and, according to a further aspect, for a use in tropical regions. Here, it is advantageous if a comparatively high long-term storage stability at elevated temperature in the range of 30–40° C. can be ensured.

However, the lithium salt of the formula (I) can also be formed quasi in situ during the preparation of the oil suspension concentrate. This is achieved, for example, by grinding, instead of the lithium salt of the formula (I), the acid of the formula (Ia) together with corresponding amounts of lithium hydroxide. Water that is released can be bound or removed. Suitable for this purpose are, for example, the water-binding agents described above as component (d3); alternatively, the water can be distilled off azeotropically, for example in the presence of toluene.

The present invention also provides the use of the oil suspension concentrates according to the invention as crop protection compositions in agriculture. This use encompasses a method for treating crops which method comprises applying an effective amount of at least one oil suspension concentrate according to the invention.

Depending on the application method used, the oil suspension concentrates according to the invention can be employed in a large number of crop and ornamental plants for eliminating undesirable plants. Suitable are, for example, the following crops:

*Allium cepa, Ananas comosus, Arachis hypogaea, Asparagus officinalis, Beta vulgaris* spp. *altissima, Beta vulagris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Ficus elastica, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

Oil suspension concentrates according to the invention are used in particular as grass herbicides, especially for crops of rice.

For this purpose, the oil suspension concentrates according to the invention are, prior to use, generally converted into a form suitable for application, by dilution in a customary manner. Preference is given to dilution with water or else aprotic solvents, for example by the tank mix method for application from an aeroplane (ULV application). Use in the form of a spray liquor preparation is preferred. Application is generally carried out by the pre-emergence or post-emergence method.

Since a virtually water-free formulation based on oil is present, application by the ULV method (ultra low volume) is also possible, for example by application from an aeroplane.

For a customary tank mix spray liquor, per ha from 0.25 to 5, preferably from 0.5 to 2.0, l of the oil suspension concentrate according to the invention are diluted with water to from 5 to 2000 l. For a ULV tank mix spray liquor, per ha from 0.25 to 10 l, preferably from 0.5 to 5 l, of the oil suspension concentrate according to the invention are diluted to from 5 to 50 l with an oil phase, preferably an oil of component (b), for example a Spraytex oil, or with water or a mixture of water and oil, in a volume ratio of from about 2:1 to 4:1. If appropriate, from 0.1% by weight to 5% by weight (based on the spray liquor) of further anionic, cationic or nonionic surfactants, auxiliaries, polymers and/or the other herbicidally active compounds mentioned above are added to the tank mix spray liquor. Examples of such surfactants and further auxiliaries have already been described above. Particular mention may be made of starch and starch derivatives, for example a starch containing carboxyl and sulfonic acid groups (Nu-Film from Union Carbide Corp.), and also spreaders and extenders, such as Vapor Guard from Miller Chemical and Fertilizer Corp.

The invention is illustrated in more detail by the examples below:

PREPARATION EXAMPLES

Reference Example 1
Lithium Salt of the Formula (I)

At 25° C., 702.78 g (0.400 mol) of a 26.5% strength solution of the cyclohexenone oxime ether (Ia) in toluene are initially charged and diluted with 229.47 g of toluene, giving a concentration of the cyclohexenone oxime ether (Ia) of 20%. 200.98 g (0.420 mol) of a 5% strength LiOH solution (calcined LiOH (98+); Chemetall) in MeOH are then added over a period of 30 min. The mixture is stirred at 25° C. for 1 h. 370.59 g of an MeOH/toluene/water mixture are then distilled off under reduced pressure at 50° C. Here, the temperature is maintained at 50° C. and the pressure is reduced, in a controlled manner, from 450 mbar to 100 mbar. The distillation time is 210 min. After the distillation has ended, 13 g of methanol are added, the mixture is stirred at room temperature for 15 min and the suspension is discharged from the stirrer vessel and applied to a pressure filter nutsch. After the filtration has ended, the stirrer vessel is rinsed with 174.00 g (200 ml) of fresh toluene and the filter cake is washed with this wash toluene. The filter cake is then washed twice with in each case 87.0 g (100 ml) of fresh toluene. The filter cake is then dried in a vacuum drying cabinet at 50° C. for 24 h. This gives 181.01 g of filter cake having a content of 98.2%. Taking this content into account, the yield is 94.1%.

Reference Example 2
Oil Suspension Concentrate by Direct Grinding (D)

About 90% by weight of component (b) and the total amount of component (c) are initially charged. The active compound component (a) is added as a solid powder (reference example 1). The formulation mixture is then made up with the remaining amount of component (b) to 1 liter. The mixture is then, at about 0° C., ground in a Dyno-mill from Bachofen by passage operation, using glass beads (0.9–1.2 mm) as grinding auxiliaries, until a cumulative sum distribution of the particle sizes is reached where about 60% of the particles have a particle size of less than 2 $\mu$m. Typically, this requires 5 passages.

Reference Example 3
Oil Suspension Concentrate by Blending from Active Compound Preconcentrate (A)

The active compound component (a) and about 30% by weight of component (b) are, as described above, ground to a preconcentrate. The preconcentrate is then initially charged, mixed with component (c) and adjusted to the desired active compound content using remaining proportions of component (b).

Examples 1 to 23:

Using Preparation Variant (D) or (A), oil suspension concentrates according to the specifications given in Table 2 below are prepared (examples 1 to 23).

TABLE 2

Active compounds and auxiliaries of certain oil suspension concentrates, stated as ["name"/"g/kg of oil suspension concentrate"], unless indicated otherwise.

| Ex. | Active compound | Component (b) | Component (c) | |
|---|---|---|---|---|
| 1 | I/75 | Me-oleate/413 Solvesso 150/208 | Aerosol OT-A/300 | A |
| 2 | I/75 | Plastomoll DOA/413 Solvesso 150/208 | Emulpon EL 20/300 | A |
| 3 | I/75 | Me-oleate/500 Glissopal 2300/61 | Aerosol OT-A/250 Emulpon EL 20/50 | D |
| 4 | I/75 | Me-oleate/500 Glissofluid A13/60 | Aerosol OT-A/250 Emulpon EL 20/50 | D |
| 5 | I/75 | Me-oleate/500 Solvesso 150/125 | Aerosol OT-A/250 Atlas G 1086/50 | A |
| 6 | I/100 | Me-oleate/500 Solvesso 150/94 | Emulan A/50 | A |
| 7 | I/100 | DBE-6/650 | Aerosol OT-A/150 Emulan A/50 | A |
| 8 | I/100 | DBE/650 | Aerosol OT-A/150 Emulpon EL 20/50 | A |
| 9 | I/100 | DBE/650 | Aerosol OT-A/150 Emulan A/50 | A |
| 10 | I/75 | Me-oleate/413 Solvesso 150/208 | Agrilan AEC 211/300 | A |
| 11 | I/75 | Plastomoll DOA/413 Solvesso 150/208 | Agrilan AEC 233/300 | A |
| 12 | I/75 | Me-oleate/413 Solvesso 150/208 | Aerosol OT-A/150 Pluronic RPE 2520/100 | A |
| 13 | I/75 | Me-oleate/500 Solvesso 150/120 | Aerosol OT-A/150 Atlox 4914/150 | A |
| 14 | I/75 | Plastomoll DOA/413 Solvesso 150/208 | Emulpon EL 20/250 Plurafac LF 131/50 | A |
| 15 | I/75 | Me-oleate/200 cyclohexanone/200 Solvesso 150/ad 11 | Aerosol OT-A/250 Emulpon EL 20/50 | A |
| 16 | I/75 | Me-oleate/200 cyclohexanol/200 Solvesso 150/ad 11 | Aerosol OT-A/250 Emulpon EL 20/50 | A |
| 17 | I/75 | Me-oleate/200 isobutanol/200 Solvesso 150/ad 11 | Aerosol OT-A/250 Emulpon EL 20/50 | A |
| 18 | I/75 | Me-oleate/200 tert-butanol/200 Solvesso 150/ad 11 | Aerosol OT-A/250 Emulpon EL 20/50 | A |
| 19 | I/75 | Me-oleate/200 n-butanol/200 Solvesso 150/ad 11 | Aerosol OT-A/250 Emulpon EL 20/50 | A |
| 20 | I/75 | Me-oleate/500 Solvesso 150/61 | Aerosol OT-A/250 Emulpon EL 20/50 | D |
| 21 | I/75 | Me-oleate/500 Spraytex oil/ad 11 | Aerosol OT-A/250 Emulpon EL 20/50 | D |
| 22 | I/75 | Me-oleate/500 paraffin oil/ad 11 | Aerosol OT-A/250 Emulpon EL 20/50 | D |
| 23 | I/150 | Me-oleate/200 Solvesso 150/ad 11 | Aerosol OT-A/250 Emulpon EL 20/50 | D |

Example 24:

436.4 g of a 34.4% strength solution of (Ia) in toluene were, with evaporation of toluene, stirred at 40° C. and 20–30 mbar in a rotary evaporator for 5 hours and then subjected to a 3-hour after-treatment at 1 mbar and room temperature. The oily residue was then taken up in twice the amount of Solvesso 150. The auxiliaries stated below, which correspond to components (b) and (c) of example 23, were then stirred in and the mixture was made up to 1 l with Solvesso 150.

| 24 | Ia/150 | Me-oleate/200 | Aerosol OT-A/250 | D |
|---|---|---|---|---|

-continued

| | Solvesso 150/ad 11 | Emulpon EL 20/50 |
|---|---|---|

The auxiliaries used in the examples above are illustrated in Table 2 below.

TABLE 2

| Name | Structure type/material | Manufacturer |
|---|---|---|
| Component (b) | | |
| Me-oleate | methyl oleate | Henkel |
| DBE-6 | dimethyl adipate | Dupont |
| DBE | dicarboxylic acid ester mixture | Dupont |
| Plastmoll DOA | di-(2-ethylhexyl) adipate | BASF |
| Glissofluid A 13 | di-(isononyl) adipate | BASF |
| Aerosol OT-A | dioctyl sodium sulfosuccinate in mineral oil distillate | Cytec Industries |
| Solvesso 150 | naphthene mixture | Shell |
| Solvesso 200 | naphthene mixture | Shell |
| Glissopal 2300 | polyisobutene | BASF |
| Spraytex oil | $C_{18}$–$C_{24}$-hydrocarbon mixture | Texaco |
| Paraffin oil | $C_{14}$-alkanemixture | BASF |
| Component (c) | | |
| Emulpon EL 20 | castor oil x 20 EO | Witco |
| Agrilan AEC 211 | alkylbenzenesulfonic acid Ca salt (with 10–15% by weight of isobutanol) | Akros |
| Emulan A | oleic acid x 5.5 EO | BASF |
| Atlas G 1086 | polyoxyethylene sorbitol hexaoleate | Unichema |
| Atlox 4914 | polyester | Unichema |
| Pluronic RPE 2520 | polypropylene oxide/ polyethylene oxide block polymer | BASF |
| Plurafac LF 131 | C8–C14-polyoxethyl butyl ether, end-capped | BASF |

Physical Properties, Stability and Emulsifying Properties

The stability of oil suspension concentrates (Examples 1 to 22) is examined in an accelerated-aging test. To this end, the samples are stored in sealed glass containers at 54° C. for 14 days. The concentration of active compound is then determined. This value, in relation to the original active compound content, is a measure for the stability of the oil suspension concentrate.

The emulsifying properties are assessed by visual scoring, similar to the method of CIPAC MT 180, in a 100 ml spray flask. The oil suspension concentrate is prepared as a 2% by weight strength mixture in water. The following assessment scale is used:

++: no cream or sediment;
+: little cream or sediment, <0.1 ml;
+/−>0.1<0.5 ml of cream/sediment;
(−)>0.5 ml of cream or sediment, inhomogeneous sample Table 3 below summarizes the stability data and the assessment of the emulsifying properties of certain oil suspension concentrates.

TABLE 3

| Ex. | Stability (% rel.) | Emulsifying properties (2%) |
|---|---|---|
| 1 | 100 | + |
| 2 | 97.0 | + |
| 3 | 95.4 | + |
| 4 | 99.5 | + |
| 5 | 92.3 | ++ |

TABLE 3-continued

| Ex. | Stability (% rel.) | Emulsifying properties (2%) |
|---|---|---|
| 6 | 98.0 | + |
| 7 | 98.9 | ++ |
| 8 | 98.4 | ++ |
| 9 | 98.8 | ++ |
| 10 | 67.1 | ++ |
| 11 | 63.5 | + |
| 12 | 88.0 | (−) |
| 13 | 87.9 | ++ |
| 14 | 89.6 | (−) |
| 15 | 92.2 | n.d. |
| 16 | 90.5 | n.d. |
| 17 | 87.8 | n.d. |
| 18 | 93.4 | n.d. |
| 19 | 88 | n.d. |
| 20 | 97.5 | ++ |
| 21 | 98 | ++ |
| 22 | 98 | + | n.d.: not determined, owing to insufficient stability of the active compound

The oil suspension concentrates according to the invention of Examples 1 to 9 and 20 to 23, in particular, have excellent storage stability. The emulsifying properties are satisfactory.

The formulations from Examples 23 and 24 were stored in 50 ml vials at 50° C. The relative residual amounts of active compound (I) or (Ia), analytically determined each case as the free acid, as shown in Table 4 below.

TABLE 4

| Ex. | Serum value | 30 d | 90 d | 180 d |
|---|---|---|---|---|
| 23 | 0.01% | 99.6 | 98.2 | 93.2 |
| 24 | 100% | 88.4 | 72.4 | 56.2 |

Accordingly, oil SC formulations according to the invention based on the active compound salt (I) have considerably better storage stability than EC formulations based on the free passage of the active compound (Ia).

Biological Properties

Outdoor trials with various herbicide combinations in rice were carried out as randomized block experiments with 3 or 4 repetitions. The area of the plots used for the experiments varied between 2 to 6 m². In each case, the products were applied using a knapsack sprayer. The knapsack sprayer was fitted with a lance having 4 or 6 flat spray nozzles. The products were applied in a volume of 300 l of water/ha. The rice crop was fertilized according to the standard recommendations. Because of the small weed population, per broadcast seeding, an additional 5–10 kg/of weeds/ha were sown manually. In experiments with strong growth of broadleaved and Cyperus weeds, bentazone or 2,4-D was applied 7 days after the application of the graminicides to prevent interactions. The development stages of the rice and the weeds were determined in accordance with the BBCH scale (Strauss R. 1994: Compendium of Growth Stage Identification Keys for Monoand Dicotyledoneus Plants. Extended BBCH-Scale. ISBN 3-9520749-0-X). Selectivity and herbicidal action were assessed in accordance with the EPPO guideline (OEPP/EPPO 1998: Guideline for the Efficacy Evaluation of Herbizides—Weeds in Paddy Rice—EPPO Standard 1/62 (2) English. In: Guidelines for the Efficacy Evaluation of Plant Protection Products. Vol. 4. Herbicides and Plant Growth Regulators).

The results of the outdoor trials that were carried out are summarized in Table 5 below.

TABLE 5

| Ex. | appl. rate [g of ai/ha] | % damage to the plants after | | | ECHCG | LEFCH |
| --- | --- | --- | --- | --- | --- | --- |
| | | 7 days | 21 days | 42 days | 42 days | 42 days |
| 20 | 38 | 2 | 4 | 3 | 96 | 98 |
| | 75 | 4 | 8 | 5 | 100 | 100 |
| 21 | 38 | 2 | 4 | 3 | 98 | 100 |
| | 75 | 4 | 14 | 9 | 100 | 100 |
| 22 | 38 | 2 | 5 | 4 | 96 | 99 |
| | 75 | 4 | 23 | 15 | 100 | 100 |

ECHCG: Echinocloa crus-galli
LEFCH: Leptochloa chinesin
appl. rate: application rate, based on the amount of active compound These experiments show that the auxiliary component (b1) according to the invention, here in the form of methyl oleate, causes relatively little damage to the crops, while having a generally good action on weeds.

We claim:

1. An oil suspension concentrate comprising
   (a1) 2-{1-[2-(4-chlorophenoxy)propoxyimino]butyl}-3-hydroxy-5-(tetrahydrothiopyran-3-yl)cyclohex-2-enone lithium salt of the formula (I)

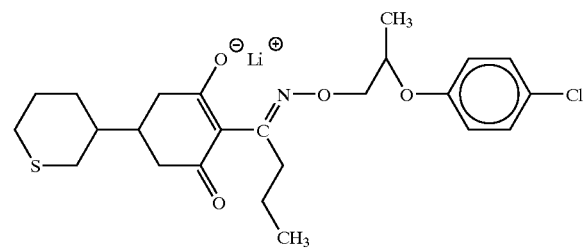

(I)

and
   at least one component selected from the group consisting of
   (b1) at least one mono- and/or dicarboxylic ester of the formula (IIa) or (IIb)

$$R^1-CO-OR^2 \quad (IIa)$$
$$R^3-O-CO-A^1-CO-O-R^4 \quad (IIb)$$

where $R^1$ is a straight-chain or branched saturated or unsaturated aliphatic radical having 6 to 30 carbons, $R^2$ is straight-chain or branched alkyl or cycloalkyl, $A^1$ is straight-chain or branched alkylene or cycloalkylene and $R^3$, $R^4$ independently of one another are straight-chain or branched saturated or unsaturated aliphatic radicals having 1 to 24 carbons;
   (c1) at least one anionic surfactant of the formula (III)

$$R^5-SO_3^- 1/n\ M^{(n+)} \quad (III)$$

where M is a mono- or divalent cation (n=1 or 2) and $R^5$ is a straight-chain or branched aliphatic or heteroaliphatic radical having 6 to 30 carbons or a ($C_6$–$C_{30}$-alkyl)aryl radical, and
   (c2) at least one nonionic surfactant of the formula (IV)

$$[R_6-CO-(EO)_x-]_y A^2 \quad (IV)$$

where $R^6$ is a straight-chain or branched saturated or unsaturated—optionally mono- or dihydroxylated—aliphatic radical having 8 to 30 carbons, the sum of all x is from zero to 100, y is from 1 to 7, $A^2$ is hydroxyl or alkyloxy if y is 1, or $A^2$ is derived from a polyol if y is from 2 to 7.

2. An oil suspension concentrate as claimed in claim 1 comprising
   (a1) the lithium salt of the formula (I) and
   (a2) at least one further herbicidal crop protection agent.

3. An oil suspension concentrate as claimed in claim 2 which comprises, as further herbicidal crop protection agent, a carboxylic acid metal salt of the formula (V)

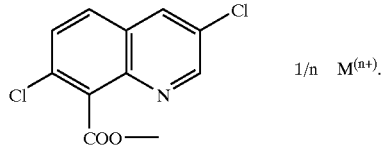

(V)

4. An oil suspension concentrate as claimed in any of the preceding claims, where the component (b1) is selected from the group consisting of $C_1$–$C_8$-alkyl esters of oleic acid, di($C_1$–$C_{12}$-alkyl) esters of adipic acid and mixtures thereof.

5. An oil suspension concentrate as claimed in any of the preceding claims comprising a component (b2) which is selected from the group consisting of at least one alkylaromatic compound from the benzene or naphthalene series which may be hydrogenated or partially hydrogenated.

6. An oil suspension concentrate as claimed in any of the preceding claims where the component (c1) is selected from the group consisting of di($C_1$–$C_{12}$-alkyl)sulfosuccinates, ($C_6$–$C_{30}$-alkyl)benzenesulfonates and mixtures thereof.

7. An oil suspension concentrate as claimed in any of the preceding claims where the component (c2) is selected from the group consisting of castor oil polyethoxylates, sorbitol polyethoxyoleates and mixtures thereof.

8. An oil suspension concentrate as claimed in any of the preceding claims comprising
   (d) at least one further component selected from the group consisting of
      (d1) lithium salts,
      (d2) antisettling agents and
      (d3) water-binding agents.

9. The use of an oil suspension concentrate as claimed in any of claims 1 to 10 as crop protection composition in agriculture.

10. The use as claimed in claim 9 as rice herbicide.

* * * * *